United States Patent
Dörre

(10) Patent No.: US 7,602,882 B2
(45) Date of Patent: Oct. 13, 2009

(54) C-ARM X-RAY APPARATUS WITH CONTROL OPTIMIZED FOR DEGREES OF FREEDOM AND METHOD

(75) Inventor: Helmut Dörre, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 78 days.

(21) Appl. No.: 11/900,833

(22) Filed: Sep. 13, 2007

(65) Prior Publication Data

US 2008/0069309 A1    Mar. 20, 2008

(30) Foreign Application Priority Data

Sep. 14, 2006  (DE) .................. 10 2006 043 144

(51) Int. Cl.
*H05G 1/54*  (2006.01)
(52) U.S. Cl. ..................... 378/117; 378/197
(58) Field of Classification Search .............. 378/98, 378/117, 193–198, 204, 210
See application file for complete search history.

(56) References Cited

U.S. PATENT DOCUMENTS 7,160,027 B2   1/2007  Bauer et al.

2002/0041654 A1 *  4/2002  Hayashi ................ 378/196
2005/0100134 A1    5/2005  Bauer et al.

FOREIGN PATENT DOCUMENTS

| DE | 4224246 C1 | 8/1993 |
|---|---|---|
| DE | 103 47 738 A1 | 9/2005 |

* cited by examiner

Primary Examiner—Courtney Thomas

(57) ABSTRACT

The invention relates to an x-ray C-arm apparatus comprising an x-ray C-arm and a control facility that moves the x-ray C-arm in at least one rotational and/or translational degree of freedom depending on a control signal received. The x-ray C-arm apparatus features a user interface with a control element connected to the x-ray C-arm. The control element is connected to the user interface and enables it to be moved with at least one rotational and with at least one translational degree of freedom. The user interface detects the movement of the control element and creates the control signal depending on the movement of the control element, with the control signal representing at least the degree of freedom and/or a direction of movement of the control element, especially a direction of movement in the degree of freedom.

15 Claims, 3 Drawing Sheets

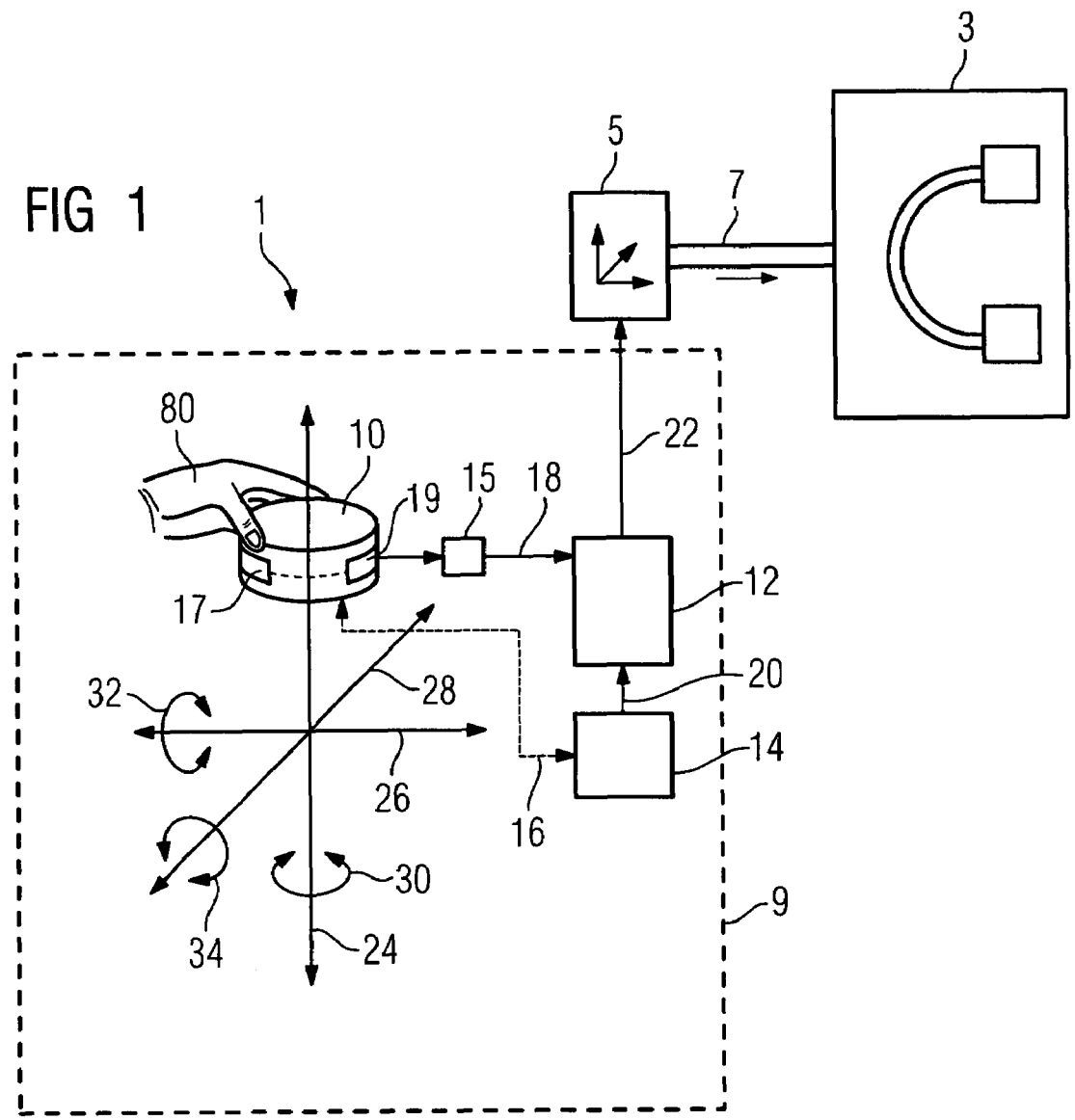

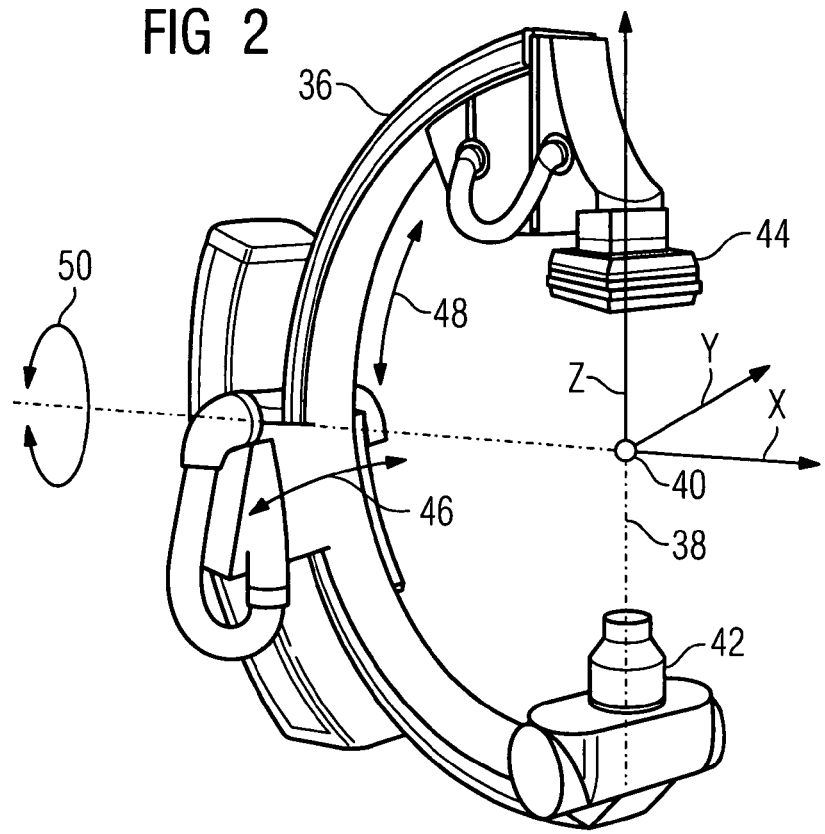
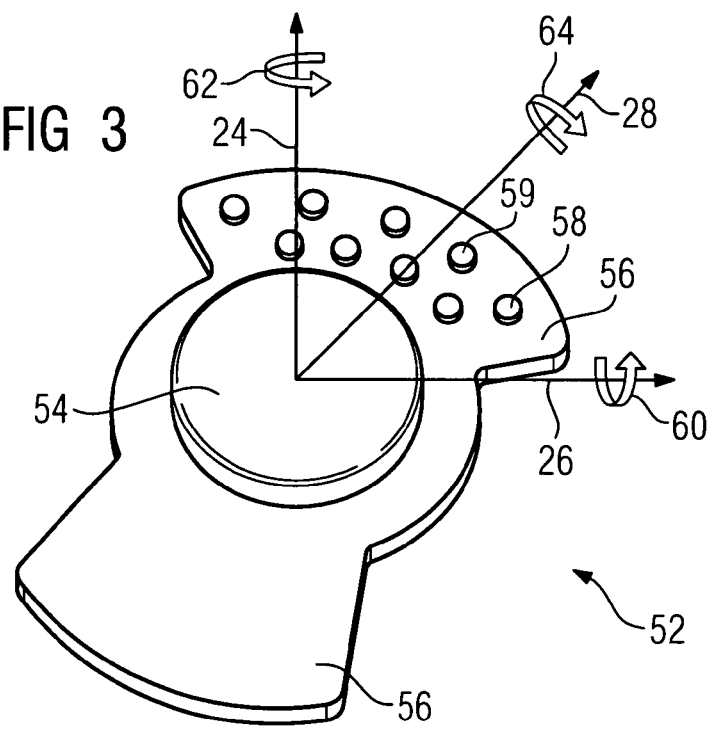

C-ARM X-RAY APPARATUS WITH CONTROL OPTIMIZED FOR DEGREES OF FREEDOM AND METHOD

CROSS REFERENCE TO RELATED APPLICATIONS

This application claims priority of German application No. 10 2006 043 144.8 filed Sep. 14, 2006, which is incorporated by reference herein in its entirety.

FIELD OF THE INVENTION

The invention relates to an x-ray C-arm apparatus. The x-ray C-arm apparatus features an x-ray C-arm and a control facility. The control facility is embodied to move the x-ray C-arm depending on a control signal received on the input side.

BACKGROUND OF THE INVENTION

With x-ray C-arm apparatus known from the prior art the control facility is connected to a user interface, with the user interface featuring a control element embodied to allow movement and the control facility being embodied to detect a movement of the control element—for example by a user of the C-arm x-ray apparatus—and to generate the control signal depending on the movement of the control element.

In this way a user can move the x-ray C-arm so that a movement of the x-ray C-arm is dependent on a movement of the control element. The user can thus control the C-arm indirectly by means of the control element. With x-ray C-arm apparatus known from the prior art the control element is embodied to enable it to swivel.

SUMMARY OF THE INVENTION

The underlying object of the invention is to specify an x-ray C-arm apparatus with an improved control facility. This object is achieved by an x-ray C-arm apparatus which has an x-ray C-arm and a control facility. The control facility is embodied to move the x-ray C-arm in at least one rotational and/or translational degree of freedom depending on a control signal received on the input side. The x-ray C-arm apparatus features a user interface with a control element connected at least indirectly to the control facility, with the control element being effectively connected to the x-ray C-arm.

The control element is connected to the user interface and embodied such that it can be moved with at least one rotational and with at least one translational degree of freedom. The user interface is embodied to detect the movement of the control element and to generate the control signal depending on the movement of the control element, with the control signal representing at least the degree of freedom and/or a direction of movement of the control element, especially a direction of movement in the degree of freedom. Such a user interface enables the x-ray C-arm to be conveniently controlled; in particular a degree of freedom of a movement of the C-arm can correspond to a prespecified degree of freedom of the movement of the control elements and/or the direction of movement.

In a preferred embodiment the control element is connected to the user interface and embodied so as to enable movement with at least two rotational and/or at least two translational degrees of freedom. This advantageously allows an x-ray C-arm to be controlled in a convenient manner.

For example the x-ray C-arm can be embodied to be moved in at least two rotational and/or at least two translational degrees of freedom depending on the control signal received on the input side. Preferably the control signal represents the at least two rotational and/or the at least two translational degrees of freedom. The rotational movement of the x-ray C-arm also preferably corresponds to the rotational movement of the control element and/or the translational movement of the x-ray C-arm corresponds to the translational movement of the control element, in particular the movement of the x-ray C-arm additionally corresponds to a direction of movement of the control element. This advantageously enables control of the x-ray C-arm to be intuitive.

In a preferred embodiment the control element is especially connected to the user interface by means of at least one spring element and embodied to be moved, with three rotational and/or three translational degrees of freedom. This advantageously allows a complete coupling to be achieved between x-ray C-arm and the control element.

The control element can for example be connected by means of at least one swivel bearing and/or slide bearing to the user interface, especially to a housing or frame of the user interface. The control element can for example be connected by means of at least one spring element to the user interface, especially to a housing or frame of the user interface.

A swivel bearing, a slide bearing or a spring element allows the control element to be moved in one degree of freedom, especially to be limited to the degree of freedom.

In an advantageous embodiment the control element is connected by means of at least one magnetic field to the user interface. To this end a housing or frame of the user interface and the control element can each feature a ferromagnet, with said magnets being arranged and polarized in relation to each other so that the control element is kept floating and can be moved against a force of the magnetic field.

The control facility is also preferably embodied to move the x-ray C-arm in three rotational and/or three translational degrees of freedom.

In an advantageous embodiment the control element can be moved in more degrees of freedom than the user interface can detect. The user interface is embodied in this embodiment to restrict, the number and/or type of the detectable degrees of freedom. This advantageously enables incorrect operations to be prevented.

One rotational movement of the x-ray C-arm in this case also preferably corresponds to a rotational movement of the control element and/or a translational movement of the x-ray C-arm corresponds to a translational movement of the control element, especially such that a spatial arrangement of the axes of rotation of the control element to each other corresponds to a spatial arrangement of axes of rotation of the x-ray C-arm to each other, and/or a spatial arrangement of axes of translation of the control element to each other corresponds to a spatial arrangement of axes of translation of the x-ray C-arm to each other.

For example the axes of rotation of the control element can form an orthogonal system and the axes of rotation of the x-ray C-arm can form a corresponding orthogonal system. For example the axes of translation of the control element can form an orthogonal system and the axes of translation of the x-ray C-arm can form a corresponding orthogonal system.

In this way for example a rotational movement of the control element, especially a nodding movement around a transverse axis, can bring about a corresponding nodding movement of the x-ray C-arm around a transverse axis. A rolling movement of the control element around a longitudinal axis can bring about a rolling movement of the x-ray C-arm around a corresponding longitudinal axis. A yaw movement of the control element around a vertical axis can bring about a yaw movement of the x-ray C-arm around a corresponding vertical axis. The names of the axes and the names of the rotational movements are chosen to allow orientation and do not rigidly define a spatial orientation of the control element in relation to a direction of gravitational acceleration, the control element can however be arranged in this way in relation to the direction of gravitational acceleration.

In an advantageous embodiment variant the user interface is embodied to detect the movement of the control element optically. For example the user interface can feature at least one luminescence diode and at least one photo diode, photo transistor or at least one photo resistor for this purpose.

The control element in this embodiment can be effectively connected to at least one beam interruption element which is arranged and embodied to interrupt a beam path, formed from at least one luminescence diode and the at least one photo diode, depending on a movement of the control element.

The user interface in this embodiment is embodied to detect the interruption of the beam path, especially a change in the current flowing through the at least one photo diode, and to generate the control signal depending on the interruption of the beam path, especially depending on the current flowing through the photo diode.

In another embodiment the user interface has a housing or a frame, with the control element being effectively connected by means of at least one spring element to the frame or the housing respectively.

The spring element is preferably embodied, depending on a compression and/or an expansion of the spring element, to alter an ohmic resistance of the spring element. The user interface is embodied in this embodiment to detect the alteration of the ohmic resistance of the at least one spring element and to generate the control signal depending on the alteration of the ohmic resistance.

In another embodiment the user interface is embodied to detect the movement of the control element magnetically. For example in this form of embodiment the control element can be effectively connected to at least one ferromagnet and the user interface can in this embodiment feature at least one Hall sensor which is arranged and embodied so as to detect the movement of the at least one ferromagnet. The user interface in this embodiment is embodied to generate the control signal depending on the movement of the at least one ferromagnet.

In a preferred embodiment the user interface features a safety element which is embodied to detect touching and/or movement, especially pushing or pulling of the safety element by a user, and to generate an enabling signal as a function of the touching and/or movement, and to output said signal on the output side. The user interface in this embodiment is preferably embodied to generate the control signal additionally depending on the enabling signal.

In this way it can advantageously be ensured that the control element is moved by a user. In this way an unintentional movement of the x-ray C-arm can advantageously be prevented. Typical forms of embodiment for a safety element are a button or a touch-sensitive surface. The touch-sensitive surface can be embodied to conduct electricity and form a part of a capacitor.

For example the user interface can be embodied to detect a connection of the touch-sensitive surface by a user to ground potential, especially to detect this capacitively.

In another form of embodiment the user interface can be sensor with at least two transistors connected in a Darlington arrangement with an input of the Darlington arrangement being connected to the touch-sensitive surface. In this embodiment a user can act like a receiving antenna and direct energy from an electromagnetic field, for example caused by power lines, onto the touch-sensitive surface.

In a preferred embodiment of the user interface a pressure point is embodied along at least one rotation path and/or along at least one translation path of the control element. A pressure point can for example be embodied such that a resistance to movement is increased along sections of a rotation and/or translation path and when or after the pressure point is overcome, a control signal corresponding to the degree of freedom can be generated by means of the control element.

The safety element can advantageously be arranged in the area of the control element or on the control element. The safety element can preferably form an area or at least two areas of a control surface which is provided to allow touch control by the user.

For example the enabling signal can be created depending on touching at least two independent touch-sensitive surfaces. This advantageously enables an accidental movement of the x-ray C-arm to be avoided. For example a control element can feature two touch-sensitive surfaces, which are arranged opposite each other such that a first touch-sensitive surface can be touched by a user's thumb and a second touch-sensitive surface by an index finger or by another finger. The control element can be embodied to be at least partly held within a user's hand. In this way a touching of the control element by a user can advantageously be detected.

In an advantageous embodiment the C-arm x-ray apparatus is embodied to continue a movement of the x-ray C-arm depending on a location of the x-ray C-arm in at least one other degree of freedom. For example the C-arm x-ray apparatus can move the x-ray C-arm, especially by means of the control device to a predetermined location depending on the control signal. From the predetermined location onwards, the control apparatus can continue the x-ray C-arm in at least one other or precisely one other degree of freedom.

For example the x-ray C-arm can be moved up to the predetermined location in a translation. From the predetermined location onwards the x-ray C-arm can be moved further in a rotation.

The invention also relates to a method for moving an x-ray -C-arm of an x-ray C-arm apparatus by means of a control element effectively connected to the x-ray C-arm, with the x-ray C-arm moving depending on a translational movement and/or a rotational movement of the control element.

In an embodiment variant of the method the x-ray C-arm is advantageously moved with at least one translational and/or with at least one rotational degree of freedom.

In an embodiment variant of the method a rotational movement of the x-ray C-arm is undertaken depending on a rotational movement of the control element.

In a preferred embodiment of the method a translational movement of the x-ray C-arm is undertaken depending on a translational movement of the control element.

Advantageously in this case a movement of the x-ray C-arm can be undertaken according to a direction and/or a sense of direction of the movement of the control element.

The previously described embodiment variants of the C-arm x-ray apparatus are based on the common idea of performing an intuitive and safe control of an x-ray C-arm by means of an improved control element.

BRIEF DESCRIPTION OF THE DRAWINGS

The invention will now be described below with reference to Figures and further exemplary embodiments.

FIG. 1 shows an exemplary embodiment for an x-ray C-arm apparatus with an x-ray C-arm and a user interface;

FIG. 2 shows an exemplary embodiment for a control element of a user interface and possible directions of movement of the control element;

FIG. 3 shows an exemplary embodiment for a user interface;

DETAILED DESCRIPTION OF THE INVENTION

Figure 4:
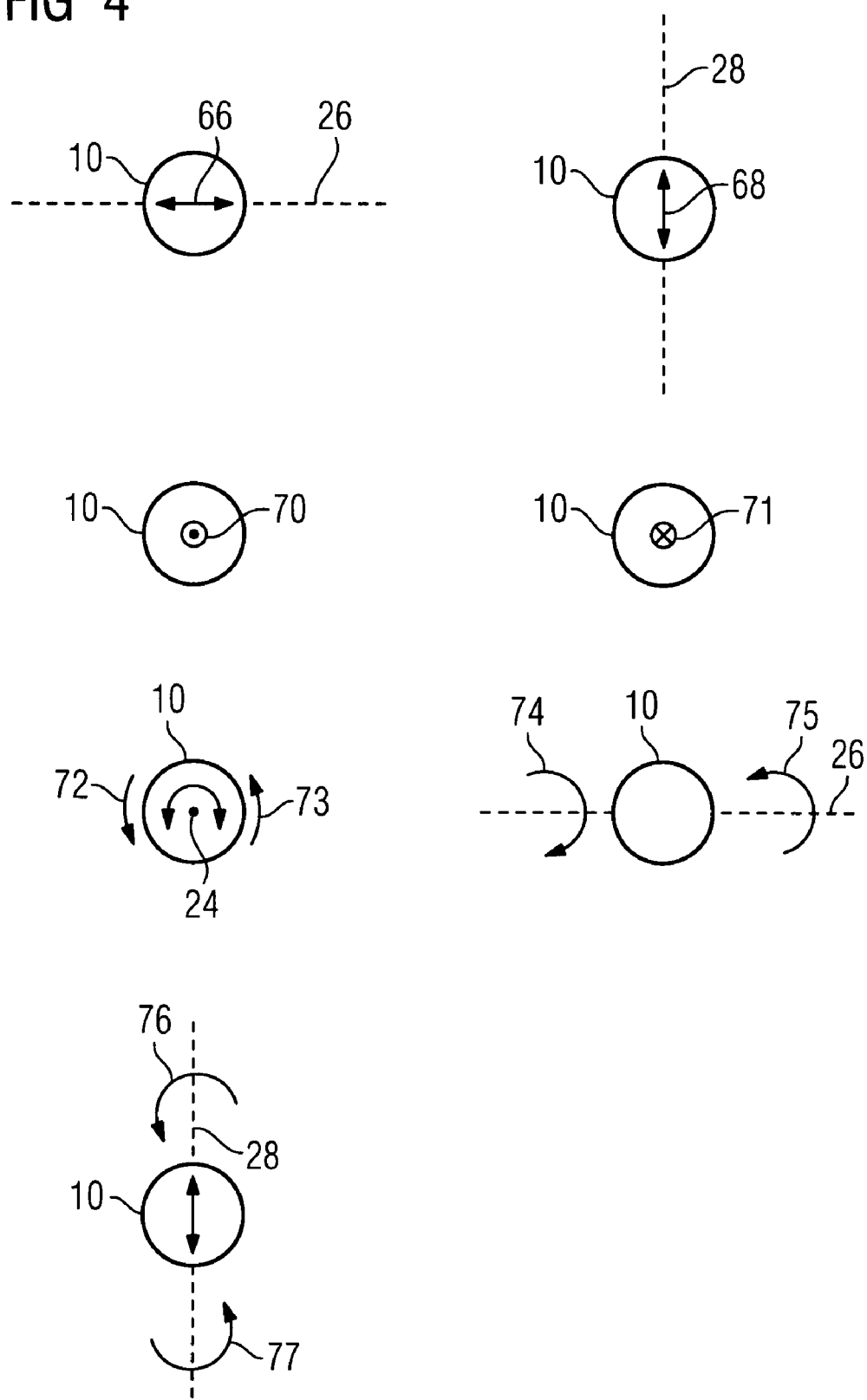
FIG. 4 shows exemplary embodiments for directions of movement of the control element in translational and/or rotational degrees of movement.

FIG. 1 shows a schematic diagram of an exemplary embodiment for an x-ray C-arm apparatus 1. The x-ray C-arm apparatus features an x-ray C-arm and a control facility. The control facility 5 is connected by means of a control mechanism 7 to the x-ray C-arm 3 and is embodied to move the x-ray C-arm 3 in at least one rotational and at least one translational degree of freedom by means of the control mechanism 7.

The C-arm x-ray apparatus 1 also features a user interface 9. The user interface 9 features a movably embodied control element 10. The user interface 9 also features a processing unit 12 which is embodied, depending on a sensor signal received on the input side and depending on an enabling signal received on the input side, to generate a control signal and output this on the output side.

The user interface 9 also features an optical sensor 14. The optical sensor 14 is embodied to detect a movement of the control element 10 by means of an optical beam 16 to generate a sensor signal corresponding to the detected movement and to output this on the output side. The optical sensor 14 is connected via a connecting line 20 to the processing unit 12. The processing unit 12 is connected on the input side via a connecting line 18 to a touch sensor 15, which is connected on the input side to a sensor surface 17 and to a sensor surface 19.

The touch sensor 15 is embodied to detect a simultaneous touching of the sensor surfaces 17 and 19 by a user and to create an enabling signal depending on the simultaneous touching and to output this on the output side via the connecting line 18 to the processing unit 12.

Also shown are a vertical axis 24, a transverse axis 26 and a longitudinal axis 28, which are each orthogonal to one another and together form an orthogonal system. The control element 10 is embodied,—for example guided by a user's hand 80, to be moved along the longitudinal axis 28 and in doing so to execute a translation movement.

The control element 10 is also embodied to be moved along a transverse axis 26 and in doing so to execute a translation movement. The control element 10 is also embodied to be moved along a vertical axis 24 and, in doing so, to execute a translation movement. The translation movements of the control element 10 can be guided in each case by a user's hand 80.

The control element 10 is also embodied to execute in a rotational degree of freedom 32 a nodding movement around the transverse axis 26. The control element 10 is also embodied to execute a yaw movement in a rotational degree of freedom 30 around the vertical axis 24. The control element 10 is also embodied to execute a rolling movement in a rotational degree of freedom 34 around the longitudinal axis 28. The rotation movements of the control element 10 can each be guided by the hand of the user 80.

The optical sensor 14 is embodied to generate the beam 16 for detecting a movement of the control element 10 and to detect the movement of the control element 10 by means if the beam 16. The optical sensor 14 can in such cases detect a translation movement along the transverse axis 26, along the longitudinal axis 28 or along the vertical axis 24 or along a combination of these. The optical sensor 14 is embodied in such cases to detect a direction of movement along at least one of the axes 26, 28 or 24 and to generate a corresponding sensor signal. The names "vertical axis 24", "transverse axis 26" and "longitudinal axis 28" are selected for orientation purposes and do not absolutely fix an orientation of the control element 10, however the control element can be arranged in this way.

The hand of the user 80 can for example move the control element 10 along the longitudinal axis 28 in a translational degree of freedom. When the hand of the user 80 touches the sensor surfaces 17 and 19 at the same time, the touch sensor 15 generates an enabling signal and sends this via the connecting line 18 to the central processing unit 12.

The optical sensor 14 can use the beam 16 to detect the translation movement along the longitudinal axis 28 and create a corresponding sensor signal and send this on the output side via the connecting line 20 to the processing unit 12. The processing unit 12, depending on the enabling signal and on the sensor signal, can generate a control signal to control the control unit 5 and output this signal on the output side.

The processing unit 12 is connected to the control unit 5 on the output side via a connecting line 22. The control unit 5 can, depending on the control signal received on the input side, use the control mechanism 7, which can for example have at least one motor for moving the x-ray C-arm, to move the x-ray C-arm in accordance with the control signal in a translational degree of freedom. If the hand of the user 80 moves the control element 10 in a rotational degree of freedom 30, 32 or 34, the control unit 5 can, in accordance with the previously described signal path, move the x-ray C-arm 3 using the control mechanism 7 in a degree of freedom corresponding to the rotational degree of freedom 34 or 30.

FIG. 2 shows a schematic diagram of an exemplary embodiment of an x-ray C-arm 36. The x-ray C-arm 36 features an x-ray transmitter 42 and an x-ray receiver 44. The x-ray transmitter 42 is arranged in the area of a first end of the x-ray C-arm 36 and the x-ray receiver 44 is arranged in the area of a second end of the x-ray C-arm 36 such that an object—for example a part of a human body—arranged in the area of an isocenter 40 can be irradiated by means of an x-ray beam emitted by means of the x-ray transmitter 42 along one direction of detection 38.

The x-ray receiver 44 is arranged and aligned so as to receive the x-ray beam emitted from the transmitter 42. The x-ray C-arm 36 is embodied to execute a translation movement along a longitudinal axis Y, along a transverse axis X, or along a vertical axis Z, or along a combination of these axes of translation.

The x-ray C-arm 36 is also embodied to execute a swivel movement along a rotational degree of freedom 46, along of a rotational degree of freedom 48 or along a rotational degree of freedom 50. A rotational movement of the x-ray C-arm 36 in the rotational degree of freedom 48 or in the rotational degree of freedom 46 is undertaken in this case around an axis of rotation, which runs through the isocenter 40.

FIG. 3 shows a schematic diagram of an exemplary embodiment for a user interface 52. The user interface 52 features a housing 56 and a control element 54 linked to the housing. The control element 54 is for example connected in a sprung manner to the housing 56, especially by means of at least one pair of opposingly polarized ferromagnets or by means of at least one spring element.

The control element 54 is embodied to execute a translation movement along a transverse axis 26, along a longitudinal axis 28 or along a vertical axis 24. The control element 54 is also embodied to execute a nodding movement in a rotational degree of freedom 60 around the transverse axis 26, a rolling movement in a rotational degree of freedom 64 around the longitudinal axis 28 or a yaw movement in a rotational degree of freedom 62 around the vertical axis 24—for example each guided by a user's hand 80—.

The user interface 52 also features keys, of which the keys 58 and 59 are shown as typical examples. The user interface 52 can for example by embodied, depending on an enabling signal generated by pressing the key 58 and depending on a movement of the control element 54, to generate a control signal for controlling the x-ray C-arm 36 shown in FIG. 2 of for controlling the control facility 5 shown in FIG. 1.

FIG. 4 shows a schematic exemplary embodiment for directions of movement of the control element 10 in translational and/or rotational degrees of freedom. If the control element 10 senses a translational movement 66 along the transverse axis 26, the x-ray C-arm 36 shown in FIG. 2 can execute a corresponding movement along the transverse axis X. If the control element 10 senses a translational movement 68 along the transverse axis 28, the x-ray C-arm 36 shown in FIG. 2 can execute a corresponding movement along the transverse axis Y. The control element 10 can also be moved along a vertical axis in direction 70, especially pulled. This can for example bring about a movement of the x-ray C-arm along a vertical axis Z in a corresponding direction.

The control element 10 can also be moved along a vertical axis in an opposite direction 71 to the direction 70, especially pushed. This can for example bring about a movement of the x-ray C-arm along a Z-axis shown in FIG. 2—in the opposite direction to the direction produced by moving the control element 10 in the direction 70.

In another embodiment a movement of the control element 10 along a vertical axis in direction 71 can cause an enabling signal to be created.

The control element 10 can also be moved around the vertical axis 24 shown in FIG. 1 in direction of rotation 72 or in a direction of rotation 73 opposite to the direction of rotation 72. A movement of the control element 10 along the direction of rotation 72 or 73 can for example bring about a rotation of the x-ray C-arm 36 shown in FIG. 2 around the Z-axis. In this case a direction of rotation of the rotation of the x-ray C-arm 36 can be a function of a rotation of the control element 10 in the direction of rotation 72. A rotation of the control element 10 in the direction of rotation 73 can bring about an inverse rotation of the x-ray C-arm 36.

The control element 10 can also be rotated around a longitudinal axis 28 in a direction of rotation 76 or in an opposing direction of rotation 77. The rotation of the control element 10 in the direction of rotation 76 can cause a rotation of the x-ray C-arm 36 in direction of rotation 48 around the Y axis. The rotation of the control element 10 in the direction of rotation 77 can bring about a rotating x-ray C-arm 36 in a direction of rotation which is opposite to the rotation of the x-ray C-arm 36 brought about by the rotation of the control element 10 in direction of rotation 76.

The control element 10 can also be rotated around the transverse axis 26 in a direction of rotation 74 or around the transverse axis 26 in a direction of rotation 75 opposite to the direction of rotation 74. The rotation of the control element 10 in direction of rotation 74 can bring about a rotation of the x-ray C-arm 36 shown in FIG. 2 around the X-axis shown in FIG. 2. A rotation of the control element 10 around the transverse axis 26 can also, depending on a local positioning of the x-ray C-arm 36, bring about a rotation of the x-ray C-arm 36 around the Y-axis in the rotational degree of freedom 48. That can for example occur if the x-ray C-arm 36 surrounds an end area of a patient bed coming from the front side of the patient bed, in which case a longitudinal direction of the patient bed can run in parallel to the X-axis.

The invention claimed is:

1. A C-arm x-ray apparatus, comprising:
   an x-ray C-arm;
   a control device that moves the x-ray C-arm in accord with a control signal when the control device simultaneously receives an enabling signal from a second, user activated device; and
   a user interface comprising a control element connected to the control device that detects a movement of the control element and generates the control signal depending on the movement of the control element,
   wherein the movement of the x-ray C-arm is executed according to a direction of movement of the control element, and
   wherein a spatial arrangement of axes of translation of the control element correspond to a spatial arrangement of axes of translation of the x-ray C-arm, and axes of rotation of the control element correspond to a spatial arrangement of axes of rotation of the x-ray C-arm.

2. The C-arm x-ray apparatus as claimed in claim 1, wherein the control element moves in at least one rotational degree of freedom and in at least one translational degree of freedom.

3. The C-arm x-ray apparatus as claimed in claim 1, wherein the movement of the control element is optically detected by the user interface.

4. The C-arm x-ray apparatus as claimed in claim 1, wherein the movement of the control element is magnetically detected by the user interface.

5. The C-arm x-ray apparatus as claimed in claim 1, wherein the x-ray C-arm is moved with at least one other degree of freedom depending on a location of the x-ray C-arm.

6. The C-arm x-ray apparatus as claimed in claim 1, wherein the user interface comprises an additional touch sensitive device, wherein the operator must touch the additional touch sensitive device while operating the control element in order to generate the enabling signal.

7. The C-arm x-ray apparatus as claimed in claim 1, wherein the control element is connected to the user interface by a magnetic field.

8. The C-arm x-ray apparatus as claimed in claim 1, wherein the control element is connected to the user interface by a spring element.

9. The C-arm x-ray apparatus as claimed in claim 1, wherein the control element can be moved in more degrees of freedom than the user interface can detect.

10. The C-arm x-ray apparatus as claimed in claim 1, wherein the control element is resiliently biased in a neutral position with at least one spring, and wherein compression and expansion of the spring changes the ohmic resistance of the spring, and the change in ohmic resistance of the spring is used to generate the control signal.

11. The C-arm x-ray apparatus as claimed in claim 1, wherein the control element moves in two rotational degrees of freedom and in two translational degrees of freedom.

12. The C-arm x-ray apparatus as claimed in claim 1, wherein the control element moves in three rotational degrees of freedom and in three translational degrees of freedom.

13. A method for moving an x-ray C-arm of an x-ray apparatus, comprising:
   connecting a control element to the x-ray C-arm; and
   moving the x-ray C-arm in response to movement of the control element, wherein the movement of the x-ray C-arm is executed according to a direction of movement of the control element when an enabling signal is present, wherein a spatial arrangement of axes of translation of the control element correspond to a spatial arrangement of axes of translation of the x-ray C-arm, and axes of rotation of the control element correspond to a spatial arrangement of axes of rotation of the x-ray C-arm.

14. The method as claimed in claim 13, wherein the x-ray C-arm is moved with at least one translational and with at least one rotational degree of freedom.

15. The method as claimed in claim 13, further comprising requiring an operator to maintain contact with an additional device to enable movement of the x-ray C-arm.

* * * * *